(12) United States Patent
van Dinther et al.

(10) Patent No.: US 11,219,414 B2
(45) Date of Patent: *Jan. 11, 2022

(54) MOTION ARTIFACT REDUCTION USING MULTI-CHANNEL PPG SIGNALS

(71) Applicant: KONINKLIJKE PHILIPS N.V., Eindhoven (NL)

(72) Inventors: Cornelus Hendricus Bertus Arnoldus van Dinther, Mierlo (NL); Gerard de Haan, Helmond (NL); David Antoine Christian Marie Roovers, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 177 days.

This patent is subject to a terminal disclaimer.

(21) Appl. No.: 16/533,319

(22) Filed: Aug. 6, 2019

(65) Prior Publication Data

US 2019/0357851 A1    Nov. 28, 2019

Related U.S. Application Data (63) Continuation of application No. 15/361,233, filed on Nov. 25, 2016, now Pat. No. 10,398,383, which is a (Continued)

(51) Int. Cl.
*A61B 5/00* (2006.01)
*A61B 5/11* (2006.01)
(Continued)

(52) U.S. Cl.
CPC .......... *A61B 5/7214* (2013.01); *A61B 5/0261* (2013.01); *A61B 5/02416* (2013.01); (Continued)

(58) Field of Classification Search
None
See application file for complete search history.

(56) References Cited

U.S. PATENT DOCUMENTS

2002/0077536 A1    6/2002  Diab et al.
2003/0109791 A1    6/2003  Kondo et al.
(Continued)

FOREIGN PATENT DOCUMENTS

EP     09 47 160       *  6/1999
EP     0947160 A1       10/1999
(Continued)

OTHER PUBLICATIONS

Ghaderi et al., "Localizing Heart Sounds in Respiratory Signals using Singular Spectrum Analysis", IEEE Transactions on Biomedical Enginerring, vol. 58, No. 12, Dec. 2011, pp. 3360-3367. (Year: 2011).*

(Continued)

*Primary Examiner* — Katherine L Fernandez (57) ABSTRACT

A data processing device (100, 200) is disclosed for extracting a desired vital signal containing a physiological information component from sensor data that includes time-dependent first sensor data (PPG1) comprising the physiological information component and at least one motion artifact component, and that includes time-dependent second sensor data that is indicative of a position, a velocity or an acceleration of the sensed region as a function of time. A decomposition unit (104, 204) decomposes the second sensor data into at least two components of decomposed sensor data and, based on the decomposed second sensor data, provides at least two different sets of motion reference data in at least two different motion reference data channels. An artifact removal unit (106, 206) determines the vital signal formed from a linear combination of the first (Continued)

sensor data and the motion reference data of at least one two of the motion reference data channels.

14 Claims, 3 Drawing Sheets

Related U.S. Application Data continuation of application No. PCT/EP2015/060864, filed on May 18, 2015.

(51) Int. Cl.
 *A61B 5/1455* (2006.01)
 *A61B 5/024* (2006.01)
 *A61B 5/026* (2006.01)

(52) U.S. Cl.
 CPC ............ *A61B 5/11* (2013.01); *A61B 5/14552* (2013.01); *A61B 5/721* (2013.01); *A61B 5/7253* (2013.01)

(56) References Cited

U.S. PATENT DOCUMENTS

| | | |
|---|---|---|
| 2004/0186387 A1 | 9/2004 | Kosuda et al. |
| 2004/0193068 A1 | 9/2004 | Burton et al. |
| 2013/0070792 A1 | 3/2013 | Shoaib et al. |
| 2016/0367198 A1* | 12/2016 | Chon ............ A61B 5/02416 |
| 2018/0028075 A1 | 2/2018 | Presura et al. |

FOREIGN PATENT DOCUMENTS

| | | |
|---|---|---|
| EP | 2491856 A1 | 8/2012 |
| JP | 2013162821 A | 8/2013 |
| JP | 2013202076 A | 10/2013 |
| WO | 9932030 A1 | 7/1999 |
| WO | 2013038326 A1 | 3/2013 |
| WO | 2013038329 A2 | 3/2013 |
| WO | 2014020463 A1 | 2/2014 |
| WO | 2014020484 A2 | 2/2014 |

OTHER PUBLICATIONS

Ram et al., "A Novel Approach for Motion Artifact Reduction in PPG Signals based on AS-LMS Adaptive Filter", IEEE Transactions on Instrumentation and Measurement, vol. 61, No. 5, May 2012, pp. 1445-1457. (Year: 2012).*

Wang et al., "Artifact Reduction based on Empirical Mode Decomposition (EMD) in Photoplethysmography for Pulse Rate Detection", Conf Proc IEEE Eng Med Biol Soc., Aug. 31-Sep. 4, 2010, pp. 959-962.

Cvetkovic et al., "Wavelet transform feature extraction from human PPG, ECG, and EEG signal responses to ELF PEMP exposures: A pilot study", Digital Signal Processing, vol. 18, Available online Jun. 6, 2007, pp. 861-874.

Ram et al., "A Novel Approach for Motion Artifact Reduction in PPG Signals Based on AS-LMS Adaptive Filter", IEEE Transactions on Instrumentation adn Measurement, vol. 61, No. 5, May 2012, pp. 1445-1457.

Yadhuraj S.R, et al., "Removal of Noise in PPG Signals Using Wavelets", International Journal of Computer Science and Mobile Computing, vol. 2, Issue 6, Jun. 2013, pp. 444-451.

* cited by examiner

MOTION ARTIFACT REDUCTION USING MULTI-CHANNEL PPG SIGNALS

CROSS-REFERENCE TO PRIOR APPLICATIONS

This application is a continuation application of U.S. National Phase application under 35 U.S.C. § 371, Ser. No. 15/361,233, filed on Nov. 25, 2016, which is a continuation of International Application Serial No. PCT/EP2015/060864, filed on May 18, 2015, which claims the benefit of European Application No. 14170178.9, filed on May 28, 2014. These applications are hereby incorporated by reference herein.

FIELD OF THE INVENTION

The present invention relates to data processing device for extracting a desired vital signal, which contains a physiological information component pertaining to a subject of interest, from photoplethysmography data. It also relates to a photoplethysmography device, to a data processing method for extracting a desired vital signal, which contains a physiological information component pertaining to a subject of interest, from photoplethysmography data, and to a computer program.

BACKGROUND OF THE INVENTION

Information about cardiovascular status, such as blood oxygen saturation, heart and respiratory rates can be unobtrusively acquired by photoplethysmography (PPG) using sensors such as contact sensors or remote sensors such as a camera. A PPG technique using a remote sensor is also referred to as remote PPG.

Whether using contact sensors or remote sensors, the PPG technique is susceptible to motion-induced signal distortions, which are superimposed to the desired vital signal. Distortions of the signals ascertained by PPG also arise from motion of the subject. Motion artifact reduction in PPG data representing the detected PPG signals is a challenging task since the contribution of the motion components often exceeds the contribution of the desired vital signal by an order of magnitude. The artifacts lead to erroneous interpretation and degrade the accuracy and reliability of estimation of cardiovascular parameters.

In a number of studies the associated PPG setups were usually operated under conditions that required the subjects to be motionless. This drawback limits the capabilities of the technique in real application environments, e.g., hospital and sports.

US 2013/0070792 A1 discloses techniques for denoising of physiological signals. A signal (e.g., physiological signal) comprising at least two signal channels is decomposed using independent component analysis (ICA) into at least two independent components. Then, independent component (IC) denoising is applied to estimate which of the at least two independent components belongs to a signal space and which of the at least two independent components belongs to a noise space using a statistical metric associated with the at least two signal channels. A de-noised version of the signal is generated by preserving in the signal only one or more independent components of the at least two independent components belonging to the signal space.

WO 2014/020463 A1 describes a device and a method for extracting physiological information from electromagnetic radiation emitted or reflected by a subject. A data stream derived from detected electromagnetic radiation is received. The data stream comprises a first sequence of signal samples indicative of various spectral portions. The data stream is split into at least two deduced staggered sequences of registered signal samples. Each of the deduced staggered sequences represents a defined spectral portion and comprises indicative signal samples spaced in time. Artificial samples are generated under consideration of proximate indicative signal samples so as to at least partially replace blank spaces between the indicative signal samples. This way, a supplemented data stream is generated.

WO 2013/038326 A1 is related to a device and a method for extracting information from remotely detected characteristic signals. A data stream derivable from electromagnetic radiation emitted or reflected by an object is received. The data stream comprises a continuous or discrete characteristic signal including physiological information and a disturbing signal portion. The physiological information is representative of at least one at least partially periodic vital signal. The disturbing signal portion is representative of at least one of an object motion portion and/or a non-indicative reflection portion. A relevant frequency band of the data stream is split into at least two defined sub-bands, comprising determined portions of the characteristic signal, each of which represents a defined temporal frequency portion potentially being of interest. The sub-bands are optimized so as to derive optimized sub-bands, the optimized sub-bands being at least partially indicative of a presence of the vital signal. The at least two optimized sub-bands are combined so as to compose an optimized processed signal.

WO 99/32030 is concerned with artifact reduction in PPG by removing motion artifacts prior to digital processing. A method is disclosed, comprising the steps of emitting electromagnetic radiation at tissue at at least first and second different wavelengths, receiving the radiation at the different wavelengths after it has been transmitted through or reflected within the tissue, providing at least first and second signals which are a logarithmic measure of the received first and second radiation wavelengths and subtracting the second signal from the first signal, removing a DC component of the result of the subtraction and providing an AC component to digital sampling means, and processing the digital samples in order to provide a desired value representing a property of the tissue.

US 2002/0077536 A1 describes a method and apparatus for analyzing two measured signals that are modeled as containing primary and secondary portions. Coefficients relate the two signals according to a model. In one embodiment the method involves utilizing a transformation which evaluates a plurality of possible signal coefficients in order to find appropriate coefficients. Alternatively, the method involves using statistical functions or Fourier transform and windowing techniques to determine the coefficients relating to the two measured signals. The methods are used in blood oximetry measurements.

SUMMARY OF THE INVENTION

It is an object of the present invention to provide a data processing device that achieves an improved motion artifact reduction of PPG data.

It is another object of the present invention to provide a PPG apparatus that achieves an improved motion artifact reduction of ascertained PPG data.

It is another object of the present invention to provide a data processing method that achieves an improved motion artifact reduction of PPG data.

It is a further object of the present invention to provide a computer program that achieves an improved motion artifact reduction of PPG data.

According to a first aspect of the present invention, a data processing device is provided for extracting a desired vital signal, which contains a physiological information component pertaining to a subject of interest, from sensor data that includes time-dependent first sensor data comprising the physiological information component and at least one motion artifact component, and that includes time-dependent second sensor data that is indicative of a position, a velocity or an acceleration of the sensed region as a function of time in one or more spatial dimensions. The data processing device comprises:

a decomposition unit, which is configured to receive the second sensor data, to decompose the second sensor data into at least two components of decomposed sensor data and to provide, based on the decomposed second sensor data, at least two different sets of motion reference data in at least two different motion reference data channels, an artifact removal unit, which is configured to receive the first sensor data and the at least two different motion reference data channels and to determine and provide at its output the vital signal formed from a combination of the first sensor data and the motion reference data of at least two of the motion reference data channels.

The data processing device of the first aspect of the present invention is based on the recognition that a vital signal with strongly reduced distortions due to motion artifacts can be obtained using a combination of the first and second sensor data. Furthermore, the data processing device uses the additional recognition that a combination can achieve this effect particularly well based on a decomposition of the second sensor data, which is indicative of a position, a velocity or an acceleration of the sensed region as a function of time in one or more spatial dimensions, into at least two components of decomposed sensor data.

A further advantage of the data processing device is that it does not require the use of previously recorded sensor data or, in other words, a sensor-data history for reducing motion artifacts in the first sensor data. In this way, it is distinguished in particular from known adaptive filtering techniques which require referring to the recent past to make adaptations in a filtering of current sensor data. However, in the presence of unpredictable, instant changes of the sensor data, which may be caused by fast accelerating movements performed by the subject of interest (e.g., a user or a patient), such references to the sensor-data history lead to inferior filtering results with regard to the desired removal of motion artifacts. In contrast, the data processing of the present invention has an improved performance in this regard and is therefore particularly suited to be operated in combination with PPG apparatus for use in a hospital or in sports. This way, the data processing device of the first aspect of the present invention forms a key to an increased use of PPG apparatus in medical environments as well as every-day life.

As is known per se from PPG techniques, the sensed region is for instance a region of skin of the subject of interest. The sensed region may also comprise tissue and blood vessels arranged below the skin of the subject of interest, in particular where transmitted electromagnetic radiation is used.

In the following, embodiments of the data processing device will be described.

Embodiments of the data processing device are configured to structure the incoming time-dependent sensor data into frames containing sensor data pertaining to predetermined time spans, wherein the decomposition unit is configured to decompose the second sensor data on a frame-by-frame basis, and the artifact removal unit is configured to determine the combination of the first sensor data and the motion reference data on the frame-by-frame basis. Frames may in different embodiments either overlap in time or strictly partition the data in disjoint time intervals. In embodiments that are suitable in particular for real-time processing, a frame may represent a concatenation of the incoming sensor data and a number of seconds of sensor data from the recent past.

A frame of sensor data, such as PPG data and/or accelerometer data, is thus to be understood as a data structure containing the time-dependent sensor data pertaining to a predetermined interval (a time window) of a time base. For instance, a frame may cover a number of seconds, in particular less than 10 seconds, preferably less than 5 seconds, and for instance at least 2 seconds. These given values are exemplary and may be varied in dependence on a sampling rate of the sensor data.

In this embodiment in particular, no reference to a previously (i.e., before the currently processed frame) recorded sensor data is made for decomposing a current frame in the decomposition unit. Since the decomposition unit processes the second sensor data, it preferably does not receive, or it neglects the first sensor data pertaining to a given frame.

Preferably, in such embodiments also the artifact removal unit is configured to perform its operations on a frame-by-frame basis, using the first sensor data and the at least two different motion reference data channels provided by the decomposition unit, which belong to a given frame.

The data processing device of the first aspect is particularly suited for an implementation that performs the data processing of the incoming sensor data in real time. Embodiments of the data processing device are configured to perform the described data processing in real time.

The combination of the first sensor data and the motion reference data of at least two of the motion reference data channels, which is determined and provided by the artifact removal unit is in one embodiment, is in one embodiment a linear combination. Other forms of combinations of the first sensor data and the motion reference data of at least two of the motion reference data channels are possible and form different embodiments.

In one embodiment, the first sensor data is PPG data indicative of an amount of electromagnetic radiation reflected from or transmitted through the sensed region in at least one first spectral channel that is sensitive to blood volume variations in the sensed region. Preferably, the at least one first spectral channel includes electromagnetic radiation having a wavelength between 500 nm and 600 nm. In some variants of this embodiment, the at least one spectral channel covers wavelengths in the spectral interval between 530 nm and 570 nm, or between 540 nm and 560 nm. Preferred embodiments include the wavelength of 550 nm, which provides a particularly high sensitivity to blood volume variations.

The second sensor data, which as mentioned is indicative of a position, a velocity or an acceleration of the sensed region as a function of time in one or more spatial dimensions, may be received as being indicative of one or more different quantities, depending on the technique(s) used to record the second sensor data. Two exemplary groups of embodiments will be described in the following In one group of embodiments, the second sensor data is also PPG data. In one such embodiment, the second sensor data comprises PPG data indicative of an amount of electromagnetic radiation reflected from or transmitted through the sensed region in at least one second spectral channel that is less sensitive to blood volume variations in the sensed region than the first spectral channel. The second spectral channel may for example contain a wavelength interval around the wavelength of 650 nm (e.g. 610-700 nm), which has a relatively lower pulsatility due to blood volume variations in the skin. In other embodiments of this type, the PPG data contains second sensor data in more than one second spectral channel, for instance in two or three spectral channels. In addition to the mentioned suitable spectral channel covering a wavelength interval around the wavelength of 650 nm, a further spectral channel may be comprised in the second sensor data that covers a wavelength interval around a center wavelength shorter than 550 nm, such as for instance a center wavelength of 450 nm.

In a second group of embodiments, the second sensor data comprises accelerometer data indicative of a change of position, a velocity or an acceleration of an accelerometer located in the sensed region of the subject of interest.

Second sensor data that comprise different types of data, such as PPG data in the at least one second spectral channel and accelerometer data are used in one embodiment, which allows further increasing a reliability of motion information provided by the motion reference data to be determined by the decomposition unit.

Further groups of embodiments provide different implementations of the signal decomposition technique employed by the decomposition unit. In the following, four exemplary groups will be described. Again, a combination of the embodiments, i.e., of different signal decomposition techniques is possible.

In a first such group of embodiments, the decomposition unit is configured to filter the second sensor data with respect to its frequency components or phase components, so as to provide the at least two components of decomposed second sensor data in the form of at least two respective frequency components or at least two respective phase components of the second sensor data. In one embodiment of this first group, the second sensor data are decomposed into at least two different sets of motion reference data in at least two different motion reference data channels in such a way that the channels correspond to different frequency regions to reduce motion artifacts. By this form of decomposition the motion reference data determined allows reducing not only those motion artifacts that are most prominent, e.g. a strongest harmonic of the second sensor data, but is also able to reduce other artifacts, e.g., those caused by weaker harmonics of the second sensor data. A particular implementation of a decomposition unit that has shown to work well comprises a low-pass filter which receives the second sensor data. The low-pass filtered signal provided in one channel of the motion reference data thus covers lower frequency range of the second sensor data. In one form of this embodiment, the decomposition unit is further configured to determine a second channel of motion reference data, which covers a higher frequency range of the second sensor data, by a calculating a difference between the second sensor data and the low-pass-filtered motion reference data pertaining to the same point in the time base. As an application example, in physical exercises where there are strong periodic movements, e.g. jogging, the first and second harmonic of the motion artifacts are prominent and in the range of the heart-rate trace. An implementation of the data processing device that uses the described approach applied to second sensor data in the form of accelerometer data has shown to reduce these two harmonics effectively and allow recovering the heart-rate trace which can be used for a reliable determination of the heart rate.

In a second such group of embodiments, which may be understood as a particular case of the first group in that it provides a different phase component, the decomposition unit comprises a Hilbert transform stage that receives as input data either the second sensor data or one of the frequency or phase components of the second sensor data, and is configured to provide at its output Hilbert transform data forming a Hilbert transform of the input data. This group of embodiments is based on the recognition that a shift in phase may occur across frequency between the PPG signal(s), resulting in a motion reference data which yields a less optimal artifact reduction. To tackle this problem the motion reference signals are fed into the Hilbert transform stage to generate additional signals that are shifted in phase by $-\pi/2$ radians across frequency. The Hilbert transform data and the original second sensor data can then be provided as an input to the artifact reduction unit. This allows compensating the shift in phase across frequency between the PPG signal(s) and therefore obtaining an artifact reduction that is free from such undesired phase effects.

In a third such group of embodiments, the decomposition unit comprises a singular spectrum analysis unit, which is configured to decompose the second sensor data as a function of time using singular spectrum analysis (SSA) into a sum of different components that form at least two components of the decomposed second sensor data. SSA decomposes the second sensor data into a number of motion reference data channels which include oscillatory components, varying trends and noise. The sum of the components represented by these channels results again in the original signal. Depending on eigenvalue spectra, different embodiments use different numbers of reconstructed components in combination with the original first and second sensor data for artifact reduction. A particular example from this group of embodiments will be described further below with reference to the Figures.

In a fourth such group of embodiments, wherein the second sensor data forms a sequence of samples each allocated to a respective one of a sequence of time-base values, the decomposition unit is configured to decompose the second sensor data by generating a plurality of time-shifted components from the second sensor data, each time-shifted component being determined from the second sensor data by shifting the allocation to the time-base values by a respective predetermined number of samples. For example, a decomposition of eight signals is realized by shifting PPG data forming the second sensor data by −4, −3, −2, −1, 1, 2, 3 and 4 samples. In another example having proven to work well, the decomposition unit is configured to generate the time-shifted components from the second sensor data in the form of PPG data by shifting it by −7, −5, −3, −1, 1, 3, 5 and 7 samples.

Combinations of the described different types of signal decomposition of different ones of these four groups of embodiments are possible and allow increasing the performance of the data processing device even further. Such combinations comprise different stages of signal decomposition in accordance with a selected combination of the different embodiments. This may for instance be implemented by sequentially arranging two or more different stages of signal decomposition of different types in the decomposition unit.

In the following, different embodiments of the artifact removal unit will be described.

Advantageously, the artifact removal unit is configured to determine individual weights of the respective spectral and motion reference data channels subject to the combination using a boundary condition, which requires that a weight vector that has as its vector components the individual weights of the spectral channels and of the motion reference data channels to be selected for the combination forms an optimum of a correspondence measure indicative of a correspondence of the vital signal to a prestored normalized correlation vector.

A second aspect of the present invention is formed by an apparatus for determining a desired vital signal, which contains a physiological information component pertaining to a subject of interest, the apparatus comprising:

an emitter unit, which comprises at least one emitter which is configured to emit electromagnetic radiation in at least one spectral channel that allows determining the physiological information component;

a sensor unit, which is configured to ascertain and provide at its output first sensor data that is indicative of an amount of electromagnetic radiation reflected from or transmitted through a sensed region of a subject of interest as a function of time in at least one spectral channel that includes the physiological information component and at least one motion artifact component in a respective spectral region of the electromagnetic spectrum, and to ascertain second sensor data that is indicative of a position, a velocity or an acceleration of the sensed region as a function of time in one or more spatial dimensions; and a data processing device according to the first aspect of the present invention or one of its embodiments described herein.

The apparatus of the second aspect of the invention shares the advantages of the data processing device of the first aspect of the invention. The apparatus is advantageously based on the photoplethysmography PPG technique.

Embodiments of the apparatus that are particularly suited for use in every-day life and sports make use of PPG signals taken in different spectral ranges. Such devices can be particularly compact. In such embodiments, the emitter unit is additionally configured to emit electromagnetic radiation in at least one second spectral channel that is less sensitive to blood volume variations in the sensed region than the first spectral channel. The sensor unit is additionally configured to ascertain PPG data indicative of an amount of electromagnetic radiation reflected from or transmitted through the sensed region in the at least one second spectral channel.

Other embodiments provide, alternatively or additionally to the additional spectral channel of PPG data, an accelerometer as a part of the sensor unit. Accelerometers based on semiconductor technology are widely used in handheld device today and can be provided in very compact size.

In a third aspect of the present invention, a data processing method is provided method for extracting a desired vital signal, which contains a physiological information component pertaining to a subject of interest, from sensor data, the data processing method comprising receiving sensor data that includes time-dependent first sensor data comprising the physiological information component and at least one motion artifact component, and that includes time-dependent second sensor data that is indicative of a position, a velocity or an acceleration of the sensed region as a function of time in one or more spatial dimensions, the:

decomposing the second sensor data into at least two components of decomposed sensor data and providing, based on the decomposed second sensor data, at least two different sets of motion reference data in at least two different motion reference data channels, determining and providing as an output the vital signal formed from a combination of the first sensor data and the motion reference data of at least two of the motion reference data channels.

The data processing method of the third aspect of the invention shares the advantages of the data processing device of the first aspect of the invention.

According to an embodiment of the invention, the method further comprises ascertaining sensor data that includes time-dependent first sensor data comprising the physiological information component and at least one motion artifact component, and that includes time-dependent second sensor data that is indicative of a position, a velocity or an acceleration of the sensed region as a function of time in one or more spatial dimension.

The operating method of the fourth aspect of the invention shares the advantages of the data processing device of the first aspect of the invention.

In a fourth aspect of the invention, a computer program comprising program code means for causing a computer to carry out the steps of the data processing method of the third aspect of the invention or one of its embodiments described herein, when said computer program is carried out on a computer.

It shall be understood that the data processing device of the first aspect of the invention or claim 1, the PPG apparatus of the second aspect of the invention or claim 9, the data processing method of the third aspect of the invention or claim 13, the operating method of the fourth aspect of the invention or claim 14, and the computer program of the fifth aspect of the invention or claim 15 have similar and/or identical preferred embodiments, in particular, as defined in the dependent claims.

BRIEF DESCRIPTION OF THE DRAWINGS

In the Following Drawings

DETAILED DESCRIPTION OF EMBODIMENTS

Embodiments of the different aspects of the present invention described in the following relate to an application in photoplethysmography. PPG has been used widely over the past, for instance for an estimation of cardiovascular parameters. This technique has been preferred over other techniques such as a chest belt for electrocardiography (ECG) or an electronic stethoscope because the latter two are often considered as a reduction in comfort and usability. However, a motion of the subject of interest, i.e., the user or patient, during a PPG measurement generates motion artifacts in measured PPG signals. The artifacts lead to erroneous interpretation and degrade the accuracy and reliability of estimation of cardiovascular parameters. The embodiments described in the following achieve a particularly good reduction or full removal of these motion artifacts.

Figure 1:
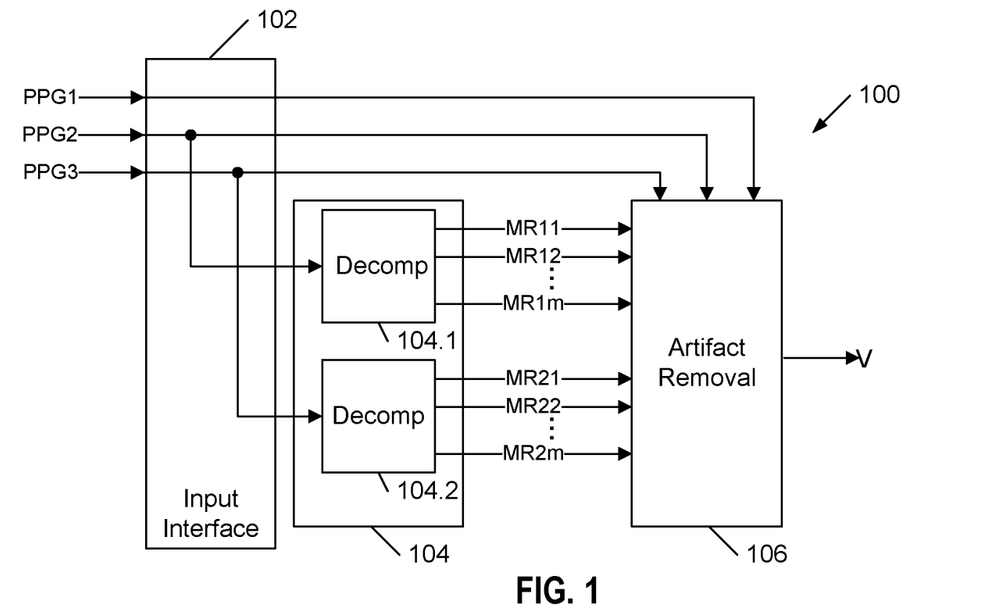
FIG. 1 shows a block diagram of a first embodiment of a data processing device.

FIG. 1 shows a block diagram of a first embodiment of a data processing device 100. The data processing device serves for extracting a desired vital signal, which contains a physiological information component pertaining to a subject of interest, from first sensor data comprising PPG data.

PPG data is data obtained by a PPG measurement before it is provided to the data processing device. The PPG data may for instance be provided in the form of sensor data generated by an optical sensor such as a photodiode or a camera, and indicate a detected amount of light emitted by a light emitter (e.g., LED or laser diode) and reflected from or, depending on the measurement setup, transmitted through a sensed region of a subject of interest as a function of time. The sensed region may be a region of the skin of the subject of interest. For instance the sensed region may be region of skin of a finger or of an earlobe.

However, the present embodiment is concerned only with the processing of the provided PPG data in order to achieve motion artifact reduction or removal.

The present exemplary embodiment of a data processing device 100 uses PPG data that is provided in the form of three different and separate streams of data, which in FIG. 1 are labeled PPG1, PPG2, and PPG3. The different streams of PPG data represent PPG measurements taken in parallel (synchronously) in three spectral channels, that is, in three spectral intervals of the electromagnetic spectrum. More specifically, a first PPG data stream PPG1, which is provided to the data processing device, comprises PPG data measured in a first spectral channel that includes the desired physiological information component and at least one motion artifact component in a respective spectral region of the electromagnetic spectrum. It is the purpose of the data processing device to extract the desired physiological information component, represented by what the present application calls the vital signal, from the measured PPG data. However, the vital signal is superimposed by the motion artifacts, and in some situations may even be hidden by motion artifacts present in the PPG data.

In particular, the spectral region covered by the first spectral channel includes the wavelength region between 540 nm and 560 nm, which provides a particularly high sensitivity to blood volume variations. A suitable spectral region for the first spectral channel is for instance 530 to 570 nm. However, a spectral channel narrower than this can also be used. The better the first spectral channel overlaps with the known characteristic optical absorption and reflection features of blood in the spectral region between 520 and 600 nm, the better is a signal-to-noise ratio of the PPG data PPG1 forming the first spectral channel.

In the language of the claims, therefore, the first PPG data stream PPG1 covering the first spectral channel provides first sensor data.

The PPG data assumed to be provided in the present embodiment further includes two other data streams, a second PPG data stream PPG2 and a third PPG data stream PPG3, which represent PPG data measured in a second and a third spectral channel. The second and third spectral channels are selected to provide PPG data that is less sensitive to blood volume variations in the sensed region than the first spectral channel. Suitable values are for example a spectral channel covering wavelengths substantially around 650 nm, e.g., 610-700 nm. This spectral channel provides a low pulsatility due to blood volume variations in the skin. Another suitable less sensitive spectral channel covers wavelengths substantially around 450 nm. Since the PPG data provided in the second and third spectral channels is less sensitive to sensitivity to blood volume variations, the PPG data PPG2 and PPG3 includes relatively less of the physiological information component and relatively more at least one motion artifact component, which is indicative of a position, a velocity or an acceleration of the sensed region as a function of time in one or more spatial dimensions.

In the language of the claims, therefore, the PPG data PPG2 in the second spectral channel and the PPG data PPG3 in the third spectral channel form second sensor data.

The data processing device 100 receives the three different PPG data streams PPG1 to PPG3 in an interface 102. The interface can be implemented by any type of data interface suitable for receiving the PPG data. It is noted that the PPG data need not be provided via three separate input ports of the interface 102. In variants, the PPG data comprising the three different PPG data streams PPG1 to PPG3 is provided to a smaller number of input ports, for example in the form of a single data stream that contains the three PPG data streams PPG1 to PPG3. In this case, the interface 102 is suitably configured to separate the PPG data streams PPG1 to PPG3.

Downstream from the interface 102, a decomposition unit 104 receives the second sensor data only, i.e., the PPG data streams PPG2 and PPG3. The decomposition unit 104 comprises two parallel decomposition stages 1041 and 104.2. A first decomposition stage 104.1 receives the second PPG data stream PPG2, and a second decomposition stage 104.2 receives the third PPG data stream PPG3. The decomposition unit 104 is configured to decompose the second sensor data into at least two components of decomposed sensor data and to provide, based on the decomposed second sensor data, at least two different sets of motion reference data in at least two different motion reference data channels. The motion reference data may be identical to the decomposed second sensor data.

In particular, in the present embodiment, motion reference data is provided by the decomposition unit 104 in the form of a number of 2 m motion reference data streams, wherein m is a positive integer. Each of the decomposition stages 104.1 and 104.2 provides a number of m motion reference data streams, which are labelled MR11, MR12, . . . , MR1$m$ for those motion reference data streams provided by the first decomposition stage 104.1, and labelled MR21, MR22, . . . , MR2$m$ for those motion reference data streams provided by the second decomposition stage 104.2. The motion reference data streams contain similar motion artifacts as the first PPG data stream PPG1, however, no a component due to blood volume variations (which may be called a heart-pulse component) or only a weak component of this type. More details of the decomposition unit 104.1 and the decomposition stages 104.2 and 104.3 will be explained further below in the context of different embodiments described with reference to FIGS. 3 to 6.

The motion reference data streams are provided to an artifact removal unit 106. The artifact removal unit 106 also receives the first sensor data, that is, the three PPG data streams PPG1 to PPG3. The artifact removal unit 106 is configured to determine and provide at its output the vital signal V formed from a combination, which in the present non-limiting example is a linear combination, of at least one of the spectral channels and at least one of the motion reference data channels.

Motion artifacts often have harmonics that differ in energy. The decomposition of the second sensor data is used in the artifact reduction unit 106 to create more degrees of freedom where the artifacts are removed from the first sensor data, PPG1. Using more degrees of freedom tackles the problem of harmonics having different energies. The motion artifact reduction can for instance be achieved by subtracting a combination, for example a linear combination of the generated motion reference data streams from the first PPG data stream PPG1.

The processing in the data processing device 100 is in particular embodiments done on a frame-by-frame basis. This provides the advantage of achieving motion artifact reduction or removal based on currently processed (frame) PPG data only, without having to refer to adaptation mechanisms for example that also require accessing previously processed PPG data.

The incoming PPG data are for instance first windowed into frames representing segments of a number of seconds. In a variant of the embodiment of FIG. 1, thus, the interface unit additionally comprises a framing unit, which is configured to receive the incoming time-dependent PPG data and to partition it into frames representing segments of the respective PPG data covering a predetermined time interval, such as for example a number of seconds.

A reconstruction of an incoming PPG data stream after the frame processing by the artifact removal unit can be achieved using an overlap-add procedure. This is a well-known technique and will therefore not be described here in more detail.

Details of the functionality and operation artifact removal unit 106 will be described further below, in particular with reference to the embodiment of FIG. 7, after the description of different embodiments of the decomposition unit 104.

Variants of the embodiment of FIG. 1 receive PPG data cover only two spectral channels, such as for example provided by the PPG data streams PPG1 and PPG2, or PPG1 and PPG3. In one such variant, the decomposition unit 104 may comprise only one decomposition stage. However, as will be described further below in more detail, the number of decomposition stages need not be in strict correspondence to the number of data steams received by the decomposition unit 104. In particular, the number of decomposition stage may be larger than the number of received data streams, so as to provide a larger number of motion reference data streams. Decomposition stages implementing different types of decomposition may be arranged sequentially and thus apply two different forms of decomposition in sequence to an incoming data stream.

Figure 2:
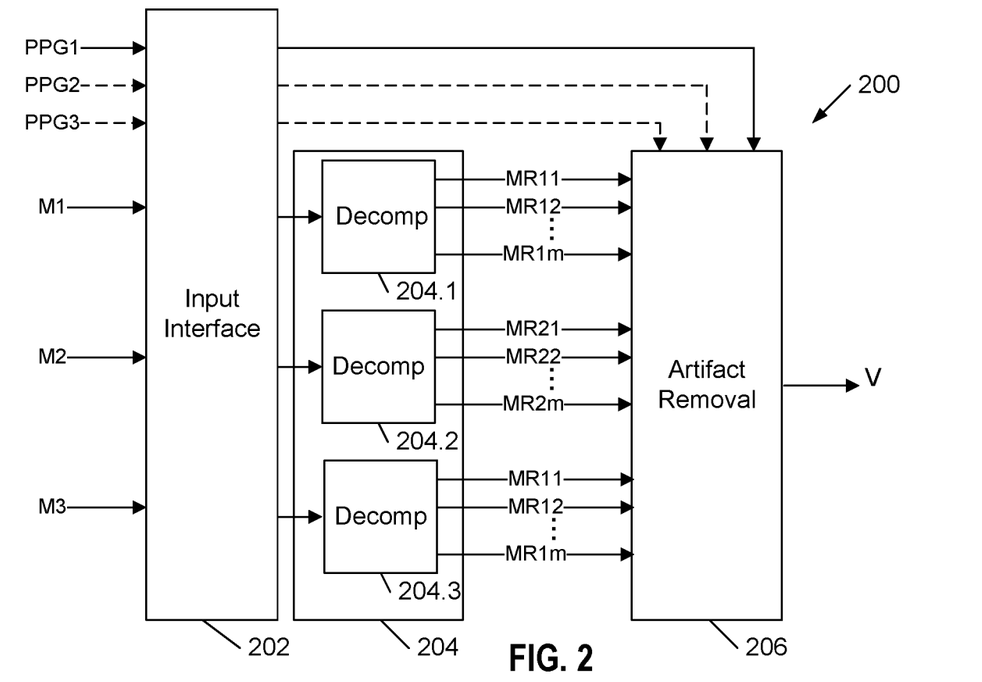
FIG. 2 shows a block diagram of a second embodiment of a data processing device.

Another variant of the embodiment of FIG. 1 will be described in the following with reference to FIG. 2. FIG. 2 shows a block diagram of a second embodiment of a data processing device 200. The data processing device 200 corresponds to that of FIG. 1 in many aspects. In particular, it also contains an interface 202, a decomposition unit 204 and an artifact removal unit 206.

As in the embodiment of FIG. 1, the first sensor data comprises the first PPG data stream PPG1. In variants of the present embodiment, the data streams PPG2 and PPG3 covering the second and third spectral channels as described with reference to FIG. 1 are also provided as additional components of the first sensor data, and therefore, like the first PPG data stream PPG1, are also directly routed from the interface 202 to the artifact removal unit 206. These variants make use of the fact that the second and third data streams PPG2 and PPG3 typically contain at least some desired physiological information. Since these data streams PPG2 and PPG3 are optionally provided, the corresponding data flow connections are indicated by dashed lines in FIG. 2.

In contrast to the embodiment of FIG. 1, data processing device 200 receives the second sensor data in the form three different streams of motion data M1, M2, and M3, which are measured by techniques other than PPG. Such motion data can for instance be determined using a sensor such as an accelerometer, which provides data concerning a position, velocity and/or acceleration.

The decomposition unit 204 of the data processing device 200 comprises three decomposition stages 204.1 to 204.3, each which provides motion reference data based on one respective stream of incoming motion data. A first decomposition stage 204.1 uses the motion data M1 for providing decomposed second sensor data in the form of m motion reference data streams MR11, MR12, ..., MR1$m$. A second decomposition stage 204.2 uses the motion data M2 for providing decomposed second sensor data in the form of m motion reference data streams MR21, MR22, ..., MR2$m$. A third decomposition stage 204.3 uses the motion data M3 for providing decomposed second sensor data in the form of m motion reference data streams MR31, MR32, ..., MR3$m$. Thus, a total number of 3 m motion reference data streams is output by the decomposition unit 204 and received by the artifact removal unit 206.

The data processing preformed by the data processing device 200 will be described in more detail further below in the context of the following embodiments.

The following description of the FIGS. 3 to 6 is concerned with different variants of the decomposition stages 104.1, 104.2 or 204.1 to 204.3 provided in the embodiments of FIGS. 1 and 2. These variants are not meant as alternatives. On the opposite, they may be combined to advantage. A decomposition unit may comprise a selection or cascade of decomposition stages and decomposition units of different type. Furthermore, use of the following variants is not restricted to these two particular exemplary embodiments formed by the data processing devices 100 and 200. Furthermore, examples of second sensor data used the following description are not meant as a limitation of any kind.

Figure 3:
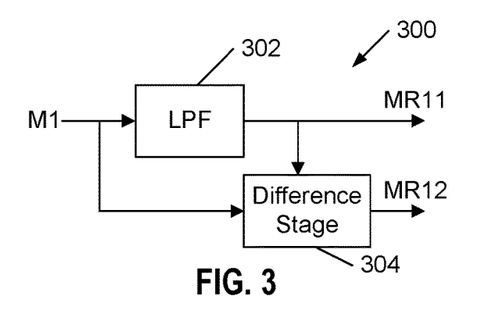
FIG. 3 shows a block diagram of a first variant of a decomposition unit for use in the first or second embodiment of the data processing device.

FIG. 3 shows a block diagram of a first variant of a decomposition stage 300 for use in a decomposition unit of embodiments of the data processing device. The decomposition unit 300 is configured to filter the second sensor data as a function of time with respect to its frequency components, so as to provide the at least two components of decomposed second sensor data as a function of time in the form of two respective frequency components the second sensor data. To this end the decomposition unit 300 comprises a low-pass filter 302. As an non-restrictive example, the second sensor data is formed by the motion data M1 mentioned in the context of FIG. 2. The low-pass filter 302 receives the time-dependent motion data M1 and provides at its output only the low-frequency components of the motion data, while the high-frequency components are blocked by the low-pass filter 302.

For determining a suitable threshold frequency, the harmonics stemming from movement should be taken into account. For instance, motion artifacts caused by jogging exhibit periodic components which lie around 80 bpm (80/60 Hz) and have an octave component at 160 bpm (160/60 Hz). A suitable threshold frequency in this case may be selected in the between 80 and 160 bpm, such as for instance at 120 bpm (120/60 Hz).

The low-pass filtered motion data is provided as a first set of motion reference data MR11. A second set of motion reference data MR12 is provided at the output of a difference stage 304, which receives at its inputs the motion data M1 and the low-pass filtered motion data provided at the output of the low-pass filter 302 and provides as its output a quantity depending on the difference between the two inputs. This second set of motion reference data MR12 is thus used to operate in the higher frequency range. Thus, the motion data M1 is decomposed by the decomposition stage 300 into two sets of motion reference data MR11 and MR12 in such a way that the data are 'forced' to operate in different frequency regions to reduce motion artifacts.

Without this decomposition the motion signals can reduce only those motion artifacts that are most prominent, e.g. the strongest harmonic, and are not able to reduce the other artifacts, e.g. the weaker harmonics. In exercises where there are strong periodic movements, e.g. jogging, the first and second harmonic of the motion artifacts are prominent and in the range of the heart-rate trace. Using this approach in combination with accelerometer signals reduces these two harmonics effectively.

Figure 4:
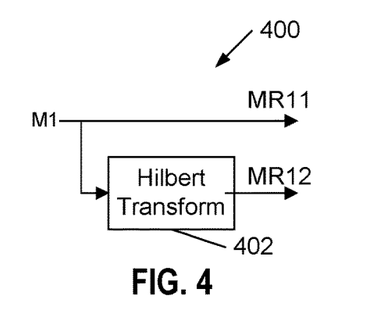
FIG. 4 shows a block diagram of a second variant of a decomposition unit for use in embodiments of a data processing device according to the present invention.

FIG. 4 shows a block diagram of a second variant of a decomposition stage 400 for use in a decomposition unit of embodiments of a data processing device according to the present invention. A shift in phase may occur across frequency between the first sensor data, i.e., one or more channels of PPG sensor data, and motion data. This undesired effect yields a less optimal artifact reduction. To tackle this problem, a Hilbert transform stage 402 is used. The Hilbert transform stage 402 receives as input data the second sensor data, as is shown in FIG. 4 by way of example for the motion data M1. In a variant, one of the frequency or phase components of the second sensor data (cf. the embodiment of FIG. 3) is provided as an input to the Hilbert transform stage 402. That is, in this variant the Hilbert transform stage 402 is arranged in sequence with the low-pass filter 302 or the difference stage 304.

The Hilbert transform stage is configured to provide at its output Hilbert transform data forming a Hilbert transform of the input data. This way, (additional) motion reference data is generated that is shifted in phase by $-\pi/2$ radians across frequency. The Hilbert transformed motion reference data MR12 and the original motion data M1 as the other set MR12 of motion reference data are then fed to the artifact reduction unit, where it can be used to used to generate a phase-shifted version of a motion reference signal by $\theta$ radians. This is achieved by a combination, such as for instance a linear combination of the Hilbert transformed signal MR12 and its original signal M1. This will be explained in further detail with reference to FIG. 7 below.

Figure 5:
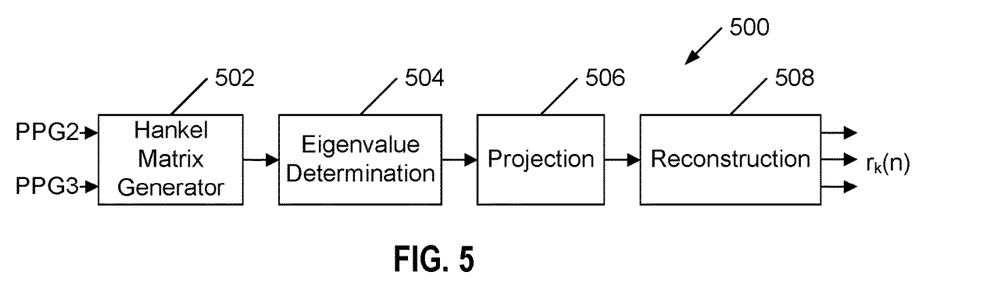
FIG. 5 shows a block diagram of third variant of a decomposition unit for use in embodiments of a data processing device according to the present invention.

FIG. 5 shows a block diagram of third variant of a decomposition stage 500 for use in a decomposition unit in embodiments of a data processing device according to the present invention. The decomposition stage 500 comprises a singular spectrum analysis (SSA) unit, which is configured to decompose the received second sensor data, such as the PPG data PPG2 and PPG3 as a function of time using SSA into a sum of different components that form at least two components of the decomposed second sensor data. SSA decomposes the received second sensor data into a number of reconstructed components which include oscillatory components, varying trends and noise. The sum of these components results again in the original signal. Depending on the eigenvalue spectra a number of reconstructed components are chosen in combination with the original signal for artifact reduction.

The following steps are used to compute the reconstructed components from a mean corrected segment of a motion reference signal, say s(n) with $n \in \{1, \ldots, N\}$. Based on an embedded dimension K and the definition $L:=N+1-K$, a $L \times K$ Hankel matrix $S=[s_0, s_1, \ldots, s_K]$ is formed in a Hankel forming unit 502. Here, $s_k$ are column vectors with elements $s_k:=[s(k), s(k+1), \ldots, s(k+L-1)]^T$. Based on the determined Hankel matrix S, an eigenvalue determination unit 504 determines eigenvalues $\lambda_1 \geq \lambda_2 \geq \ldots \geq \lambda_K \geq 0$ and eigenvectors $v_1, \ldots, v_K$ of the covariance matrix $S^T S$. A projection unit 506 projects S onto the eigenvectors $A:=SV$, where A is a matrix containing the principal components $a_k$ as columns and V a matrix with eigenvectors $v_k$ as columns. The reconstructed components $r_k(n)$ are determined in a component reconstruction unit 508 by determining $$r_k(n) := \frac{1}{M_n} \sum_{m=L_n}^{U_n} a_k(n-m+1)v_K(m),$$

with $(M_n, L_n, U_n) = (1/n, 1, n)$ for $1 \geq n \geq M-1$, $(M_n, L_n, U_n) = (1/M, 1, M)$ for $M \geq n \geq K$ and $(M_n, L_n, U_n) = (1/(N-n+1), n-N+M, M)$ for $K+1 \geq n \geq N$.

Experiments show that the present SSA embodiment works well for instance for N=128 at a sample rate of 16 Hz, and K=24. It is noted that a window length of 24 samples encompasses at least one complete period of a heart pulse.

Figure 6:
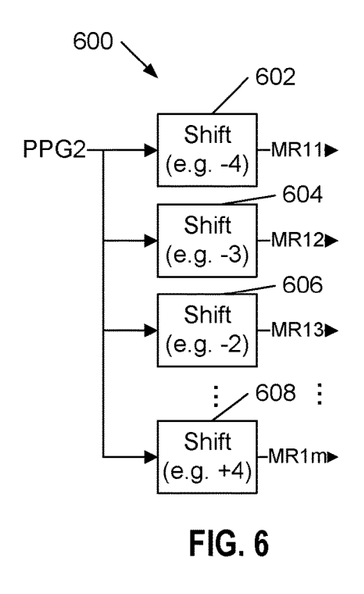
FIG. 6 shows a block diagram of a fourth variant of a decomposition unit for use in embodiments of a data processing device according to the present invention.

FIG. 6 shows a block diagram of a fourth variant of a decomposition unit 600 for use in embodiments of a data processing device according to the present invention. In the decomposition unit 600, the second sensor data, such as in the present example the second PPG data stream PPG2, is decomposed into m sets of motion reference data MR11, MR12, MR13, ..., MR1m by shifting the PPG data samples by different amounts k of samples, $k \in Z$. To this end, m shifting stages are provided, from which the first three shifting stage 602, 604, 606 and the last shifting stage 608 are shown in FIG. 6. For example, a decomposition into eight signals is realized by shifting the PPG data stream PPG2 by $-4, -3, -2, -1, 1, 2, 3$ and $4$ samples. An embodiment tested in experiments shows that artifact reduction works well by shifting PPG data by $-7, -5, -3, -1, 0, 1, 3, 5$ and $7$ samples. The zero-shift component may be obtained directly from the second PPG data stream PPG2 and thus need not be passed through a shifting stage.

In the following, further embodiments will be explained that differ in their respective artifact removal unit. Reference is made to FIG. 7, which shows a block diagram of an embodiment of an artifact removal unit for use in embodiments of a data processing device according to the present invention. For the purpose of the description to follow, the desired artifact reduced PPG signal is denoted as s(t), and a sampled signal, i.e., a desired set of artifact reduced PPG data, is denoted as s(k).

In a first embodiment of the artifact removal unit 700, weights w are computed by a weight determination stage 702 for the received first sensor data and the motion reference data such that the artifact reduced sampled PPG data is constructed in a vital signal construction stage 704 as follows:

$$s(k) = W_0 x_0(k) + W_1 x_1(k) + \ldots + W_L x_L(k)$$

Here, $L = N \cdot M$, $x_0(k)$ is the first sensor data PPG1, and $x_1(k), \ldots, x_K(k)$ are the are the motion reference data provided by the decomposition unit. The weights $W_i$ are computed solving a system of linear equations $$X^T X w = b,$$

where $X = [x_0, x_1, \ldots, x_L]$ is a K×L matrix with $x_i = [x_i(1), x_i(2), \ldots, x_i(K)]^T$. The vector w contains the weights $W_i$, and the elements of the prestored normalized correlation vector b, which is stored in a memory 706, represent the a priory predicted normalized correlations among the vectors $x_i$.

In one variant, $b = [1, 0, \ldots, 0]$ for zero correlation is predicted between the vital sign and the motion reference signals.

Figure 7:
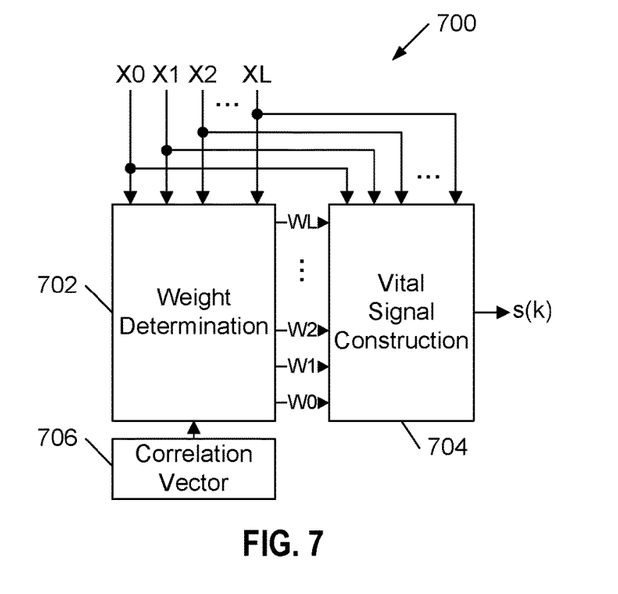
FIG. 7 shows a block diagram of an embodiment of an artifact removal unit for use in embodiments of a data processing device according to the present invention.

A second embodiment of the artifact removal unit 700, which has the same general structure as the previous embodiment and will therefore be described with continued reference to FIG. 7, is based on the embodiment of FIG. 2. Additional PPG data PPG2 of a longer wavelength, e.g. 650 nm, is fed into the artifact reduction module in this variant. This data PPG2 is closely related to PPG1 containing similar motion artifacts, but has a lower pulsatility. As in the first embodiment of FIG. 7 weights are computed by solving a system of linear equations. The a priori predicted normalized correlation vector is $b = [C, aC, 0, \ldots, 0]$, $\|b\| = 1$, where C provides the normalized correlation between the desired vital signal and PPG1, and aC, a<1 provides the correlation between the desired vital signal and PPG2. In this case $x_0(t)$ and $x_1(t)$ are the first sensor data comprising the PPG data PPG1 and PPG2 and $x_1(t)$, $l \in \{2, \ldots, L+1\}$ the motion reference data. Experiments have shown that a value of a=0.1 works well for motion artifact reduction. The parameter C is used to normalize the vector b and is computed from a given value of a and a given norm. In the exemplary case of a=0.1 and the L2 norm, $C = 1/\sqrt{1^2 + 0.1^2}$.

A third embodiment of the artifact removal unit 700, which has the same general structure as the previous embodiment and will therefore be described with continued reference to FIG. 7, and is also based on the embodiment of FIG. 2. Further Additional PPG data PPG3 of a shorter wavelength, e.g. 450 nm, is fed into the artifact reduction module in this variant in addition to the PPG data PPG1 and PPG2. As in first and second embodiments a prestored a priory correlation vector is used, extended with a correlation between the vital sign and PPG3: $b = [C, aC, bC, \ldots, 0]$, $\|b\| = 1$, with 1>b>a. In this case, $x_0(t)$, $x_1(t)$, and $x_2(t)$ correspond to the first sensor data, and are formed by the PPG data PPG1, PPG2, and PPG3, respectively. The motion reference data is $x_1(t)$, $l \in \{3, \ldots, L+2\}$. Experiments have shown that a value of a=0.1 and b=0.5 works well for motion artifact reduction.

Further sets of PPG data representing more than three different spectral channels may be used in other variants. As in the embodiments described an a priory correlation vector is composed extended with correlations between the vital signal and the (decomposed) sets of PPG signals In a fourth embodiment of the artifact removal unit 700, which forms a variant of the first embodiment, has the same general structure and will thus also be described with continued reference to FIG. 7, the dimensionality of the matrix $X^T X$ is reduced by one in comparison with the first embodiment of the artifact removal unit 700. In this embodiment, the normalized correlation vector is $b = [1, 0, \ldots, 0]$. For this case the problem can be formulated as follows:

$$X^T X w = b,$$

with $X = [x_1, \ldots, x_L]$ and $b = X^T x_0$. The artifact reduced PPG data is then $$s(k) = x_0(k) - (w_1 x_1(k) + \ldots + w_L x_L(k)).$$

In a fifth embodiment of the artifact removal unit, which is used in an embodiment of a data processing device comprising decomposition unit 500, the same general structure of the artifact removal unit 700 of FIG. 7 can be used. Experiments show that suitable prestored correlation vector $[C, a_1 C, a_2 C, \ldots a_n C]$ has the components $a_1 = c$, $a_2 = c \cdot \alpha_1$, $\ldots a_n = c \cdot a_{n+1}$, with $\alpha_i = \lambda_i / \lambda_1$, wherein $\lambda_i$ are the eigenvalues computed from the SSA method. For the case n=5 a value of $c \approx 1/20$ can be used to achieve good motion artifact reduction.

In a sixth embodiment of the artifact removal unit, which is used in an embodiment of the data processing device that has a decomposition unit using decomposition stages of the type shown in FIG. 6, the normalized correlation vector $[C, a_1 C, a_2 C, \ldots a_n C]$ can be chosen as follows: $a_i = c \cdot \cos(k_i \varphi)$, where $h_i \in z$, $t \in [1, \ldots, n]$ is a number equivalent to the sample shift in $x_i$, and a phase $\varphi = 2\pi F/f$, where F is a default pulse rate in Hz and the sample rate in Hz. Experiments have shown that this method works well with $c \approx 1/20$, F=2, and $k_i = [0, 1, -1, 3, -3, 5, -5, 7, -7]$. A further improvement could be possible by predicting F from the current frame instead of using a default value for the expected pulse-rate F. A suitable parameter for predicting F is for instance indicative of a motion rate estimated from the current frame.

Figure 8:
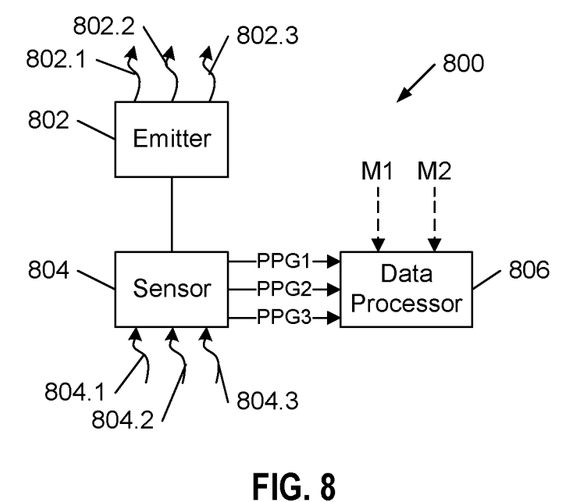
FIG. 8 shows a block diagram of a PPG apparatus according to an embodiment of the present invention.

FIG. 8 shows a block diagram of a PPG apparatus 800 according to an embodiment of the present invention. The for PPG apparatus serves for determining a desired vital signal, which contains a physiological information component pertaining to a subject of interest. The PPG apparatus 800 comprises an emitter unit 802, which comprises at least one emitter which is configured to emit electromagnetic radiation in at least one spectral channel that allows determining the physiological information component. In the PPG apparatus 800, three different light emitters operating in different spectral channels are indicated by arrows 802.1, 802.2, 803.3.

A sensor unit 804, using for example three sensors 804.1, 804.2, 804.3 is configured to ascertain and provide at its output first sensor data PPG1 that is indicative of an amount of electromagnetic radiation reflected from or transmitted through a sensed region of a subject of interest as a function of time in at least one spectral channel that includes the physiological information component and at least one motion artifact component in a respective spectral region of the electromagnetic spectrum, and to ascertain second sensor data PPG2, PPG3 that is indicative of a position, a velocity or an acceleration of the sensed region as a function of time in one or more spatial dimensions. The PPG apparatus further comprises a data processing device 806 in accordance with one of the embodiments of the data processing device described herein, for instance with reference to the FIGS. 1 to 7 above.

Figure 9:
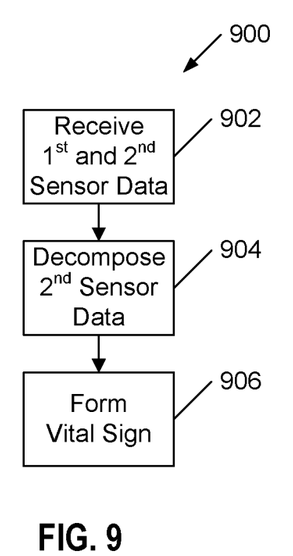
FIG. 9 shows a flow diagram of an embodiment of a data processing method according to the present invention.

FIG. 9 shows a flow diagram of an embodiment of a data processing method 900 according to the present invention. The data processing method 900 serves for extracting a desired vital signal, which contains a physiological information component pertaining to a subject of interest, from sensor data.

In a step 902 sensor data is received that includes time-dependent first sensor data comprising the physiological information component and at least one motion artifact component. The sensor data also includes time-dependent second sensor data that is indicative of a position, a velocity or an acceleration of the sensed region as a function of time in one or more spatial dimensions.

In a step 904, the second sensor data is decomposed into at least two components of decomposed sensor data. Based on the decomposed second sensor data, at least two different sets of motion reference data is provided in at least two different motion reference data channels.

In a step 906, the vital signal formed from a linear combination of the first sensor data and the motion reference data of at least one two of the motion reference data channels it is determined and provided as an output.

Figure 10:
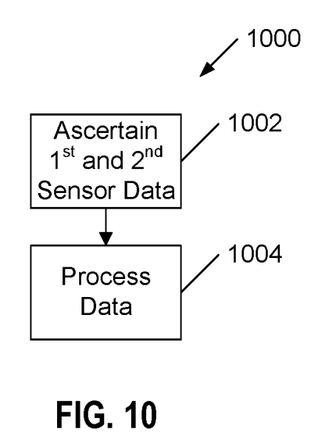
FIG. 10 shows a flow diagram of an embodiment for operating a PPG apparatus according to the present invention.

FIG. 10 shows a flow diagram of an embodiment for operating a PPG apparatus according to the present invention. The method comprises ascertaining sensor data in a step 1002. As described before, the sensor data includes time-dependent first sensor data comprising the physiological information component and at least one motion artifact component, and it includes time-dependent second sensor data that is indicative of a position, a velocity or an acceleration of the sensed region as a function of time in one or more spatial dimension. In a step 1004, the data processing method 900 is performed.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single stage or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A data processing device for using motion artifact reduction to extract a desired vital signal, which comprises a physiological information component pertaining to a subject of interest, from sensor data that includes:
   time-dependent first sensor data, obtained from a sensed region in a first spectral channel that is sensitive to blood volume variations, and comprising the physiological information component and at least one motion artifact component, and
   time-dependent second sensor data in the form of photoplethysmography (PPG) data, obtained simultaneously with the first sensor data,
      wherein the PPG data is indicative of a position, a velocity, or an acceleration of the sensed region as a function of time in one or more spatial dimensions;
   the data processing device comprising:
   a decomposition circuit configured to:
      receive the second sensor data,
      decompose the second sensor data as a function of time into a set of different components that form at least two components of the decomposed second sensor data, and
      provide, based on the decomposed second sensor data, at least two different sets of motion reference data in at least two different motion reference data channels; and
   an artifact removal circuit configured to:
      receive the first sensor data and the at least two different motion reference data channels, and to
      determine and provide at its output the vital signal formed from a combination of the first sensor data and the motion reference data of at least two of the motion reference data channels;
   wherein the decomposition circuit is further configured to filter the second sensor data as a function of time with respect to its phase components, to provide the at least two components of decomposed second sensor data as a function of time in the form of at least two respective phase components of the second sensor data that are phase shifted relative to each other.

2. The data processing device of claim 1, wherein the artifact removal circuit is configured to determine individual weights of the respective spectral and motion reference data channels subject to the combination using a boundary condition that requires that a weight vector that has as its vector components the individual weights of the spectral channels and of the motion reference data channels to be selected for the combination forms an optimum of a correspondence measure indicative of a correspondence of the vital signal to a prestored normalized correlation vector (b).

3. The data processing device of claim 1, which is configured to structure the time-dependent first and second sensor data into frames containing sensor data pertaining to predetermined time spans, wherein the decomposition circuit is configured to decompose the second sensor data on a frame-by-frame basis, and the artifact removal circuit is configured to determine the combination of the first sensor data and the motion reference data on the frame-by-frame basis.

4. The data processing device of claim 1, wherein the at least two respective phase components of the second sensor data are phase shifted by $-\pi/2$ radians relative to each other.

5. The data processing device of claim 1, wherein the PPG data is indicative of an amount of electromagnetic radiation reflected from or transmitted through the sensed region in at least one second spectral channel that is less sensitive to blood volume variations in the sensed region than the first spectral channel.

6. An apparatus for using improved motion artifact reduction to determine a desired vital signal, which contains a physiological information component pertaining to a subject of interest, the apparatus comprising:
   an emitter circuit comprising at least one emitter that is configured to emit electromagnetic radiation in at least a first spectral channel that allows determining the physiological information component;

a sensor circuit that is configured to:
ascertain and provide at its output first sensor data that is indicative of an amount of electromagnetic radiation reflected from or transmitted through a sensed region of a subject of interest as a function of time in the first spectral channel that includes the physiological information component and at least one motion artifact component in a respective spectral region of the electromagnetic spectrum, and
ascertain second sensor data in the form of photoplethysmography (PPG) data that is indicative of a position, a velocity or an acceleration of the sensed region as a function of time in one or more spatial dimensions;

a decomposition circuit configured to:
receive the second sensor data,
decompose the second sensor data as a function of time into a set of different components that form at least two components of the decomposed second sensor data, and
provide, based on the decomposed second sensor data, at least two different sets of motion reference data in at least two different motion reference data channels; and an artifact removal circuit that is configured to:
receive the first sensor data and the at least two different motion reference data channels, and to
determine and provide at its output the desired vital signal formed from a combination of the first sensor data and the motion reference data of at least two of the motion reference data channels;

wherein the decomposition circuit is further configured to filter the second sensor data as a function of time with respect to its phase components, so as to provide the at least two components of decomposed second sensor data as a function of time in the form of at least two respective phase components of the second sensor data that are phase shifted relative to each other.

7. The apparatus of claim 6, wherein:
the emitter circuit is additionally configured to emit electromagnetic radiation in the at least one second spectral channel that is less sensitive to blood volume variations in the sensed region than the first spectral channel, and
the sensor circuit is configured to ascertain data indicative of an amount of electromagnetic radiation reflected from or transmitted through the sensed region in the at least one second spectral channel.

8. The apparatus of claim 6, wherein the at least two respective phase components of the second sensor data are phase shifted by $-\pi/2$ radians relative to each other.

9. The apparatus of claim 6, wherein the PPG data is indicative of an amount of electromagnetic radiation reflected from or transmitted through the sensed region in at least one second spectral channel that is less sensitive to blood volume variations in the sensed region than the first spectral channel.

10. A data processing method for using improved motion artifact reduction to extract a desired vital signal, which contains a physiological information component pertaining to a subject of interest, from sensor data, the data processing method comprising:
receiving sensor data in the form of photoplethysmography (PPG) data that includes time-dependent first sensor data, obtained from a sensed region in a first spectral channel, comprising the physiological information component and at least one motion artifact component, and that includes time-dependent second sensor data in the form of PPG data, obtained simultaneously with the first sensor data, wherein the PPG data is indicative of a position, a velocity, or an acceleration of the sensed region as a function of time in one or more spatial dimensions,
decomposing the second sensor data as a function of time into a set of different components that form at least two components of the decomposed second sensor data and
providing, based on the decomposed second sensor data, at least two different sets of motion reference data in at least two different motion reference data channels; and
determining and providing as an output the vital signal formed from a combination of the first sensor data and the motion reference data of at least two of the motion reference data channels;
wherein the decomposing further comprises filtering the second sensor data as a function of time with respect to its phase components, so as to provide the at least two components of decomposed second sensor data as a function of time in the form of at least two respective phase components of the second sensor data that are phase shifted relative to each other.

11. The data processing method of claim 10, wherein the at least two respective phase components of the second sensor data are phase shifted by $-\pi/2$ radians relative to each other.

12. The data processing method of claim 10, wherein the PPG data is indicative of an amount of electromagnetic radiation reflected from or transmitted through the sensed region in at least one second spectral channel that is less sensitive to blood volume variations in the sensed region than the first spectral channel.

13. A non-transitory computer-readable medium comprising program code that, when executed by a computer, causes the computer to:
receive sensor data in the form of photoplethysmography (PPG) data that includes time-dependent first sensor data, obtained from a sensed region in a first spectral channel, comprising the physiological information component and at least one motion artifact component, and that includes time-dependent second sensor data in the form of PPG data, obtained simultaneously with the first sensor data, wherein the PPG data is indicative of a position, a velocity, or an acceleration of the sensed region as a function of time in one or more spatial dimensions,
decompose the second sensor data as a function of time into a set of different components that form at least two components of the decomposed second sensor data and
provide, based on the decomposed second sensor data, at least two different sets of motion reference data in at least two different motion reference data channels; and
determine and provide as an output a vital signal formed from a combination of the first sensor data and the motion reference data of at least two of the motion reference data channels;
wherein the program code causes the computer to decompose the second sensor data by filtering the second sensor data as a function of time with respect to its phase components, so as to provide the at least two components of decomposed second sensor data as a function of time in the form of at least two respective phase components of the second sensor data that are phase shifted relative to each other.

14. The medium of claim 13, wherein the PPG data is indicative of an amount of electromagnetic radiation reflected from or transmitted through the sensed region in at least one second spectral channel that is less sensitive to blood volume variations in the sensed region than the first spectral channel.

\* \* \* \* \*